US006837855B1

(12) United States Patent
Puech

(10) Patent No.: US 6,837,855 B1
(45) Date of Patent: Jan. 4, 2005

(54) USE OF AN ULTRASONIC TRANSDUCER FOR ECHOGRAPHIC EXPLORATION OF HUMAN OR ANIMAL BODY TISSUES OR ORGANS IN PARTICULAR OF THE EYEBALL POSTERIOR SEGMENT

(76) Inventor: Michel Puech, 11, rue Bertin Poirée, 75001 Paris (FR)

( * ) Notice: Subject to any disclaimer, the term of this patent is extended or adjusted under 35 U.S.C. 154(b) by 0 days.

(21) Appl. No.: 09/581,515

(22) PCT Filed: Dec. 18, 1998

(86) PCT No.: PCT/FR98/02788

§ 371 (c)(1),
(2), (4) Date: Jul. 27, 2000

(87) PCT Pub. No.: WO99/32036

PCT Pub. Date: Jul. 1, 1999

(30) Foreign Application Priority Data

Dec. 18, 1997 (FR) .............................. 97 16071

(51) Int. Cl.⁷ ................................. A61B 8/06
(52) U.S. Cl. .................................... 600/452
(58) Field of Search ................ 600/407–471; 351/201; 356/632; 604/22; 128/898, 915, 916; 73/620–633

(56) References Cited

U.S. PATENT DOCUMENTS

| | | | | |
|---|---|---|---|---|
| 4,276,491 A | * | 6/1981 | Daniel | 310/317 |
| 4,883,061 A | * | 11/1989 | Zeimer | 356/632 |
| 5,293,871 A | * | 3/1994 | Reinstein et al. | 600/442 |
| 5,331,962 A | * | 7/1994 | Coleman et al. | 600/444 |
| 5,369,454 A | * | 11/1994 | Reinstein et al. | 351/201 |
| 5,412,854 A | * | 5/1995 | Lockwood et al. | 29/25.35 |
| 5,551,432 A | | 9/1996 | Iezzi | 128/660.09 |
| 5,666,954 A | * | 9/1997 | Chapelon et al. | 600/439 |
| 5,776,068 A | * | 7/1998 | Silverman et al. | 600/443 |

OTHER PUBLICATIONS

Pavlin, C. et al., Ultrasound Biomicroscopy of the Eye, *Ultrasound of the Eye and Orbit*, 2002, pp. 223–235, U.S.A.

Pavlin, C. et al., Ultrasound Biomicroscopy in the Assessment of Anterior Scleral Disease, *American Journal of Ophthalmology*, Nov., 1993, vol. 116, pp. 628–635.

Foster, F.S. et al., Ultrasound Backscatter Microscopy of the Eye In Vivo, *IEEE 1990 Ultrasonics Symposium Proceedings*, Dec. 4–7, 1990, vol. 3, pp. 1481–1484.

Pavlin, C. et al., Ultrasound Biomicroscopy of Anterior Segment Structures in Normal and Glaucomatous Eyes, *American Journal of Ophthalmology*, Apr., 1992, vol. 113, pp. 381–389.

Basic Physics of High–Frequency Ultrasound Imaging, *Ultrasound Biomicroscopy of the Eye*, 1995, pp. 3–16, Springer–Verlag, New York.

F. S. foster et al., "Ultrasound Backscatter Microscopy Of The Eye in Vivo.", Preceedings of the Ultrasonics Symposium, vol. 3, PP. 1481–1484, Dec. 4–7, 1990, XP–000289858.

(List continued on next page.)

Primary Examiner—Ali Imam
(74) Attorney, Agent, or Firm—Foley & Lardner LLP

(57) ABSTRACT

The present invention relates to the use of a high frequency ultrasound transducer with long focal length for making a device and for implementing a method of echographic exploration of tissue or organs of the human or animal body. More particularly, the invention relates to using an ultrasound transducer having a nominal excitation frequency greater than 20 MHz, preferably lying in the range 50 MHz to 80 MHz, with long focal length, greater than 10 mm, preferably about 25 mm, for making a device for echographic exploration of the eyeball, in particular of the posterior segment of the eyeball, and more particularly of the macular region.

35 Claims, 6 Drawing Sheets

OTHER PUBLICATIONS

Ronald H. Silverman et al., "Three-dimensional High-frequency Ultrasonic Parameter Imaging of Anterior Segment.", Ophthalmology, vol. 102, No. 5, pp. 837–848, May, 1995, XP-002074921.

Charles J. Pavlin et al., "Subsurface Ultrasound Microscopic Imaging of the Intact Eye.", Ophthalmology, vol. 97, No. 2, pp. 244–250, Feb., 1990, XP-002074922.

Tello et al., "Ultrasound Biomicroscopy in Pseudophakic Malignant Glaucoma," *Ophthalmology*, Sep. 1993, pp. 1330–1334, vol. 100, No. 9.

*Ultrasound Biomicroscopy of the Eye*, "Chapter 1, Basic Physics of High-Frequency Ultrasound Imaging," pp. 3–16.

Pavlin et al., "Ultrasound Biomicroscopy of Anterior Segment Structures in Normal and Glaucomatous Eyes," *American Journal of Opthalmology*, Apr. 15, 1992, pp. 381–389, vol. 113, No. 4, © American Journal of Opthalmology.

Pavlin et al., "Ultrasound Biomicroscopy in the Assessment of Anterior Scleral Disease," *American Journal of Opthalmology*, Nov. 1993, pp. 628–635, vol. 116, © American Journal of Opthalmology.

Foster et al., "Ultrasound Backscatter Microscopy of the Eye In Vivo," *IEEE 1990 Ultrasonics Symposium Proceedings*, Dec. 4–7, 1990, pp. 1481–1484, vol. 3, B.R. McAvoy (Ed.).

* cited by examiner

10mm

500μm

500 μm    500 μm

USE OF AN ULTRASONIC TRANSDUCER FOR ECHOGRAPHIC EXPLORATION OF HUMAN OR ANIMAL BODY TISSUES OR ORGANS IN PARTICULAR OF THE EYEBALL POSTERIOR SEGMENT

The present invention relates to the use of a high frequency and long focus ultrasound transducer for making a device to implement an echographic method of exploring tissues or organs of the human or animal body, specifically the eyeball, in particular the posterior segment of the eyeball, and more particularly the macular region.

C. Pavlin and F. Foster were the first to publish a series of works on exploring the eye by means of a high frequency echographic device (50 MHz).

Since their first publications in 1990 concerning a laboratory device (C. J. Pavlin, M. D. Sherar, F. S. Foster: Subsurface ultrasound microscopic imaging of the intact eye, Ophthalmology 97: 244, 1990 and C. J. Pavlin, M. Easterbrook, J. J. Hurwitz, K. Harasiewicz, F. Stuart Foster: Ultrasound biomicroscopy in the assessment of anterior scleral disease, American Journal of Ophthalmology, November 1993; 116: 628–635), much work has continued this innovation, with the appearance of a device sold by Humphrey-Zeiss under the name Ultrasound BioMicroscope (UBM). Many authors have since used the technique to multiply publications on two-dimensional (2D) exploration of the anterior segment in vivo.

Under the prompting of J. Coleman, several articles by R. Silverman, N. Allemann, and D. Reinstein have gone beyond the stage of mere 2D imaging and have associated it with an analysis of frequency content.

The principal innovation of that high frequency echography lies in the fact that its axial and lateral resolution is about 50 $\mu$m, making it possible to explore superficial ocular membrane envelopes in vivo in a manner comparable with a macroscopic histological section.

The main limitation of the technique lies in the shallow depth of analysis of experimental or commercial systems. Most publications relate to windows of 4 mm in width and 4 mm in depth, thereby restricting observations to the anterior segment of the eye, without reaching the posterior face of the lens, or restricting observations to the very front portion of the posterior segment while moving the transducer over the pars plana. With increasing frequency of the ultrasound beam, there is increasing attenuation of the beam by the media through which it passes.

Although it would thus appear to be unrealistic to hope to obtain 50 micron resolution on the retina by using transducers at 50 MHz to 80 MHz, our aim has been to achieve a significant improvement in the resolution of images of the posterior segment. When the eye,is compared to a camera, the anterior segment acts as an objective lens with its share of optical problems, while the posterior segment determines visual potential by means of the special tissue constituted by the retina which acts as the photographic film.

The need to improve the quality of retina exploration is associated with two important concepts:
  at present and in spite of encouraging research, it is not possible to transplant the retina, whereas essential elements of the anterior segment can be replaced (corneal transplant, cataract operation); and
  the highest concentration of retinal visual cells is situated in a very small area known as the macula. Visual capacity depends on its integrity.

As a general rule, it is explored by optical means, such as biomicroscopy and angiography. Nevertheless, such exploration is limited by problems associated with the transparency of the media of the eye (cataracts, hemorrhages) and at best they provide only a plane image of the retina.

B-mode echography provides a sectional image of the retina and explores vitro-retinal relationships more precisely. However, although the resolution of 10 MHz devices is sufficient to explore the retina as a whole, it does not provide an analysis of the macular region that is as fine as an angiograph.

Furthermore, in order to perform an examination of the anterior segment by echography at 10 MHz, it is necessary to implement immersion with appropriate cupules so as to bring the focal zone which is situated at 23 mm onto the anterior segment.

Nevertheless, since the appearance of high frequency devices, the difference in image resolution is such that exploring the anterior segment by echography at 10 MHz has been downgraded to second-best.

The only device sold on a worldwide scale (the UBM) is a 50 MHz device which provides 2D images over a maximum depth of 4 mm and with axial resolution of 50 microns. Furthermore, that device displays a window that is restricted to a width of 4 mm, which is insufficient to explore the entire anterior segment in a single B-scan section. Options for producing 3D images and for characterizing tissue are not provided by the manufacturer.

The early work by C. Pavlin and S. Foster in 1990 was performed using a laboratory device with 50 MHz to 100 MHz probes in order to produce a 2D image of the anterior segment. Using that device, various pieces of work were published concerning exploration of the anatomy and the physiology of the anterior segment (C. J. Pavlin, J. A. McWhae, F. S. Foster: Ultrasound biomicroscopy of anterior segment tumors, ophthalmology 99: 1222, 1992, and C. Tello, T. Chi, G. Shepps, J. Liebmann, R. Ritch: Ultrasound biomicroscopy in pseudophakic malignant glaucoma, Ophthalmology, September 1993, Vol. 100, 9: 1330–1334), and in particular the irido-corneal angle and its morphological variations in glaucoma pathologies were studied. Several publications gave images of tumors of the iris, with B-scan sections at a resolution of 50 microns to 60 microns, enabling the echostructure of those lesions to be displayed, and also making it possible to define their limits better (C. J. Pavlin, J. A. McWhae, J. A. McGowan, F. S. Foster: Ultrasound biomicroscopy of anterior segment tumors, Ophthalmology 99: 1222, 1992 and L. Zografos, L. Chamot, L. Bercher: Contribution of ultrasound biomicroscopy to conservative treatment of anterior uveal melanoma, Klin. Monast. Augen., 1996; 208(5): 414–417).

The same authors have shown that access to the anterior segment with high resolution makes it possible to monitor patients after cataract surgery including monitoring the position of an intraocular implant, for example. Similarly, after an operation for glaucoma, the ability to verify the effectiveness of surgical acts constitutes great progress.

The commercial version of that device (Zeiss-Humphrey's UBM) has provided the basis for very many international publications, such as those by C. Tello on the physiology of pigment glaucoma and of malignant glaucoma (C. Tello, T. Chi, G. Shepps, J. Liebmann, R. Ritch: Ultrasound biomicroscopy in pseudophakic malignant glaucoma, Ophthalmology, September 1993, Vol. 100; 9: 1300–1334).

J. Coleman's team used a research device with a 60 MHz transducer on the basis of which R. Silverman and D. Reinstein published work in 1992 and 1993 (D. Z. Reinstein, R. H. Silverman, S. L. Trokel, D. J. Coleman: Cornealpachymetric topography, Ophthalmology, March 1993; Vol.

103, 3: 432–438, and D. S. Reinstein, R. H. Silverman, M. J. Rondeau, D. J. Coleman: Epithelial and corneal measurements by high frequency ultrasound digital signal processing, Ophthalmology, January 1994; Vol. 101, 1: 140–146) concerning improvements to exploring the cornea using signal processing, e.g. making it possible to make a map of the cornea showing the thicknesses of the various layers thereof at a resolution of 2 microns.

That team was already one of the most advanced in tissue characterization of ocular tumors by 10 MHz echography during the 70s and 80s (D. J. Coleman, F. L. Lizzi: Computerized ultrasonic tissue characterization of ocular tumors, American Journal of Ophthalmology, 1983; 96: 165–175), so it was natural that with the work of N. Allemann, the first publications on quantitative analysis of the anterior segment at high frequency came from the same laboratory in 1993 (N. Allemann, W. Chamon, R. H. Silverman, D. T. Azar, D. Z. Reinstein, W. J. Stark, D. J. Coleman: High frequency ultrasound quantitative analysis of corneal scarring following excimer laser keratectomy, Arch. Ophthalmol., 1993; 111: 968–973, and N. Allemann, R. H. Silverman, D. Z. Reinstein, D. J. Coleman: High frequency ultrasound imaging and special analysis in trauma to hyphema, Ophthalmology, September 1993; Vol. 100, 9: 1351–1357).

In 1995, R. Silverman published a 3D reconstruction of back-scattered parametric images obtained at 50 MHz of various pathologies of the anterior segment (R. H. Silverman, et al.: Three-dimensional high frequency ultrasonic parameter imaging of anterior segment pathology, Ophthalmology, 1995, 102, 837–843).

A search through the literature on the question of analyzing the posterior segment by high frequency echography has found only four publications, all performed using a UBM on the most anterior portion of the posterior segment:

in 1994, T. Boker (T. Boker, M. Spitznas: Ultrasound biomicroscopy for examination of the sclerotomy site after pars plana vitrectomy, American Journal of Ophthalmology, 1994: 15; 118(6); 813–815) published a study of the sclerotomy site after pars plana vitrectomy;

in 1995, C. Azzolini (C. Azzolini, L. Pierro, M. Condenotti, F. Bandello, R. Brancato: Ultrasound biomicroscopy following the intraocular use of silicone oil, International Ophthalmology 1995-96, 19(3): 191–195) imaged the presence of intra-vitreous silicone residue in the anterior portion of the vitreous cavity;

in 1996, L. Zografos (L. Zografos, L. Chamot, L. Bercher: Contribution of ultrasound biomicroscopy to conservative treatment of anterior uveal melanoma, Klin. Monast. Augen, 1996; 208(5): 414–417) published a UBM study of 55 cases of uvea melanomas situated in contact with or close to the ciliary body. The conclusion of that work showed that the high attenuation of the high frequency ultrasound signal limits the use of a UBM to structures situated in the direct vicinity of the wall of the eye. Nevertheless, the contribution of high frequency echography in monitoring uvea melanomas after conservative treatment was seen to be considerable; and in 1997, A. Minamoto (A. Minamoto, K. E. Nakano, S. Tanimoto: Ultrasound biomicroscopy in the diagnosis of persistent hypotony after vitrectomy, American Journal of Ophthalmology, 1997; 123(5): 711–713) studied the separation of the ciliary body situated at the junction between the anterior segment and the posterior segment in the event of hypotony after vitrectomy.

Numerous publications relate to studying the posterior segment in 10 MHz echography, in particular with the macular region being explored.

A recent review of the international literature has found no publication concerning exploration of the macular region by echography at a frequency greater than that of the 10 MHz probes commonly used.

The originality of our work lies in improving the resolution with which the macula is analyzed, thereby making it possible to improve in vitro 2D iconography and opening the way to producing 3D images.

Quite surprisingly, it has been found that high frequency echographic analysis of the posterior segment of the eyeball, which has been considered as being impossible with existing devices because of their penetration limit at a depth of 4 mm to 5 mm in tissue, can in fact be performed by using a 50 MHz probe focused at about 25 mm. It is thus possible to analyze the posterior segment of the eyeball and in particular the macular region under excellent conditions by means of the present invention.

That is why the present invention relates to using an ultrasound transducer having a nominal excitation frequency greater than 20 MHz, preferably lying in the range 50 MHz to 80 MHz, with long focal length, greater than 10 mm, and preferably about 25 mm, to make a device for echographic exploration of tissues or organs of the human or animal body, specifically the eyeball, in particular the posterior segment of the eyeball and more particularly the macular region, and also tissues situated behind the eyeball such as the oculomotor muscles, eye socket fat, and the optic nerve.

As an example of tissues or organs suitable for being explored in the context of the present invention, mention can be made of the various layers of the skin, the muscles, and the tendons, the thyroid, the liver, and the pancreas.

The invention also relates to the use of an ultrasound transducer moved over the pars plana to prevent the ultrasound beam being absorbed by the lens of the eye, when it is desired to explore the posterior segment of the eyeball and tissues situated behind said eyeball.

Preferably, the ultrasound transducer is moved over the pars plana to avoid absorption of the ultrasound beam by the lens of the eye.

Finally, the present invention also extends to a device for echographic exploration comprising a high frequency transceiver system (20 MHz to 200 MHz) coupled to an ultrasound transducer of long focal length, greater than 10 mm and preferably about 20 mm, and a system for amplifying and storing the radiofrequency signal as played back after exploration, preferably associated with a system for recording the amplified signal and/or a system for processing the signal in the form of images, and/or a system for processing the signal in order to characterize tissue.

According to an advantageous characteristic of the invention, such a device comprises an ultrasound transducer implemented in the form of a probe controlled in such a manner as to move close to the anterior wall of the eye. This movement can be performed along two orthogonal axes, or it can follow an arcuate path.

The probe can be focused along a third axis orthogonal to the two orthogonal displacement axes, or it can be focused without being moved by using an electronic focusing system.

Advantageously, in the invention, the probe can be protected by a membrane of plastics material.

Figure 1A:
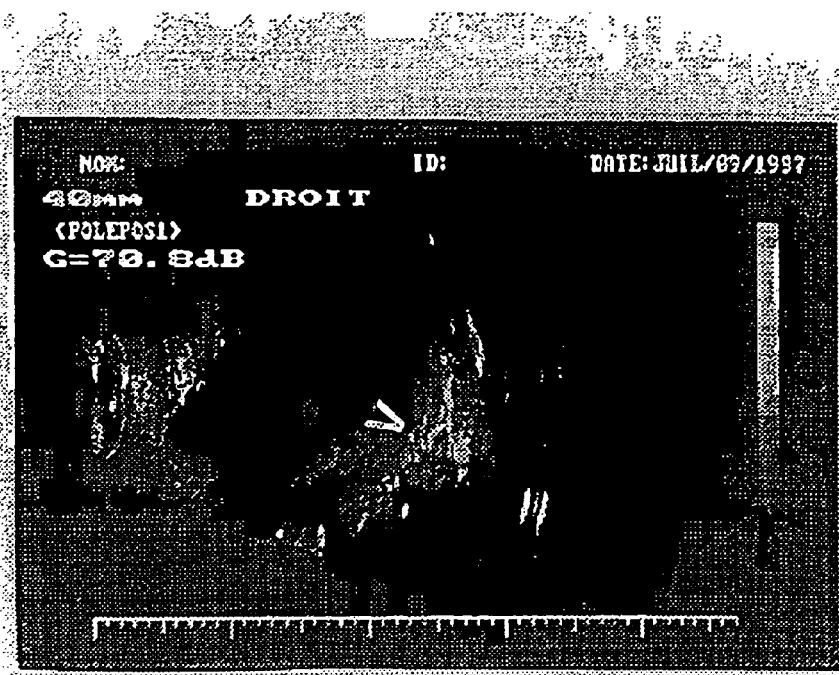
FIG. 1 is a B-scan section at 10 MHz (upper picture). The higher frequency macular image (lower picture) shows one of the first images obtained with a retinal fold.

There follows a description of the experiential equipment and methods used, in particular with reference to the accompanying drawings which show the main results observed.

Experiments were performed on various types of eyeball.

Animal Eyeballs

Initial tests were performed on the eyes of New Zealand rabbits taken immediately after euthanasia by an overdose of pentobarbital. Prior to echographic analysis, they were placed in a 9/1000 sodium chloride solution and positioned beneath the sensor by a holding device enabling the same regions of interest to be observed with different sensors. These eyeballs were used for comparing sensors with focusing on the cornea and the anterior segment.

Pigs' eyes fixed in a Bouin solution were used for the initial tests of the 50 MHz probe focused at 25 mm. Pig eyeballs are very close in size to human eyeballs and present a good model for exploring the posterior segment.

Human Eyeballs

We used six human eyeballs taken from three different deceased people who had donated their bodies to science:

eyeballs 1 and 2 came from a 75-year old man who died without any specific pathology, 2 months before the eyeballs were removed;

eyeballs 3 and 4 came from a 48-year old woman who died from a cerebral vascular accident, 14 days before the eyeballs were removed; and eyeballs 5 and 6 came from a 41-year old man who had died in a highway accident, 7 days before the eyeballs were removed.

The bodies had been conserved by freezing, which gave rise to considerable ocular artifacts on the cornea in the form of whitish corneal striations, and also on the vitreous body, in the form of intra-vitreous fibers.

Removal was performed by dissection of the limbus conjunctivae, hooking and sectioning the ocularmotor muscles without exerting traction on the eyeball itself, and then sectioning the optic nerve and the arteries and the posterior ciliary nerves using curved scissors with rounded tips.

For each pair of eyes, one of the eyeballs was placed immediately in physiological serum to be studied fresh within 1 hour of removal. After the echographic study had been finished, the fresh eye was fixed by a Bouin's solution not later than the evening on which it was removed.

The second eyeball was fixed in a Bouin's solution immediately on being removed so as to be analyzed later.

Macroscopically, all six eyeballs were of comparable appearance, with significantly low tension, requiring the eyes to be refilled with serum by means of an insulin syringe in order to return them to a spherical shape. Several cubic centimeters were injected into the vitreous cavity by an injection in the pars plana in order to avoid iatrogenic separation of the retina. Refilling the eye was then finished off by injecting serum into the anterior chamber via a self-sealing inverse corneal incision. The purpose of this injection was to prevent the lens moving forwards under the effect of the intra-vitreous injection alone, since that would have artificially closed the irido-corneal angle and flattened the anterior chamber.

Each eyeball was analyzed using conventional echography (10 MHz) and then with the ultrasound microscope (50 MHz). After being prepared, the human eyeballs were sent to the laboratory for histological analysis.

The various devices used are described briefly below.

The Ultrasound Microscope

The various polyvinylidene fluoride (PVDF) transducers were excited by a Panametrics 5900 transceiver to generate a broad band ultrasound beam.

The back-scattered ultrasound signal was amplified and then digitized on 8 bits at a sampling frequency of 400 MHz by a Lecroy 9450A oscilloscope. For each acquisition, the signal was average by the oscilloscope so as to improve the signal-to-noise ratio. Thereafter, a Dell 486 PC computer processed the A-scan and reconstructed the images in B mode, after computing the envelope of the radiofrequency signal by the Hilbert transform.

High precision (0.1 $\mu$m) stepper motors (Newport Microcontrol) moving along two orthogonal translation axes X and Y enabled three-dimensional information to be acquired. The motors were controlled by the PC.

For 3D acquisition of the posterior segment, the X displacement step was selected to be 100 $\mu$m and the Y axis step to be 200 $\mu$m.

On average, the acquisition field was 14 mm (along the X axis) by 8 mm (along the Y axis). There were 140 lines along the X axis and 40 lines along the Y axis. Each line had 2000 or 4000 points as a function of the sampling frequency (200 MHz or 400 MHz).

On average the acquisition depth was 8 mm.

The PVDF Transducers

For specific exploration of the anterior segment probes of rather short focal length were used:

a Krautkramer probe emitting at 80 MHz with a focal length of 7.5 mm, a diameter of 3 mm, and a center frequency at the focus of 60 MHz. Its axial resolution was 20 $\mu$m to 30 $\mu$m, with lateral resolution of 60 $\mu$m to 80 $\mu$m; and a Sofratest probe emitting as 33 MHz with a focal length of 12.5 mm, a diameter of 6 mm, and a center frequency at the focus of 26 MHz. Its axial resolution was 64 $\mu$m with lateral resolution of 120 $\mu$m.

To explore the retina, we used a probe having a focal length that was sufficient to enable the ultrasound beam to pass through the eyeball via the pars plana. It was a Panametrics probe emitting at 50 MHz with a focal length of 25 mm, a diameter of 6 mm, and a center frequency at the focus of 28 MHz. Its axial resolution was 70 $\mu$m with 125 $\mu$m lateral resolution at the focus in physiological serum.

Advantageously, in accordance with the invention, all of the probes were isolated from the immersion bath by a film or membrane of plastics material (of the clingfilm type), covering the transducer so as to prevent the active portion of the transducer being spoiled by coming into contact with the solution providing coupling between the eyeball and the echographic probe.

At present, in devices of known type, the probes used are plunged directly into the immersion bath without any special protection for the transducer. This requires the transducer to be sterilized before it can be used again. Such sterilization does not take place in entirely satisfactory manner.

The 10 MHz Echographic Device

Images of the retina obtained by the high frequency unit were compared with images obtained by conventional 10 MHz echography with its probe focused at 23 mm, with axial and lateral resolution of about 1 mm. This is the only kind of exploration that is available in present practice.

We iconographed the eyeballs with a Compact device (from BVI) immediately prior to acquiring data with the ultrasound microscope. That device is one of the highest performance eye echography devices presently available.

Analysis of the Frequency Response of the Signals Coming from the Posterior Wall The retinal images obtained by the ultrasound biomicroscope were analysed to discover the frequency response of the posterior wall. In order to analyze the frequency response of the posterior eye wall specifically, it was necessary to select a zone of interest.

Returning to the radiofrequency signal, ten images of each eyeball were selected randomly. The various A-scans of those images were thresholded so as to detect the first parietal peak. From this first peak, the A-scan line was shifted towards zero with the vitreous portion offset to the end of the line where a value of zero was given to all of the points. This thresholding with reduction make it possible to go from a forwardly concave parietal image in B mode to a vertical parietal image starting at zero. This step enables the analysis window to be selected better, being focused on the anterior portion of the macular wall.

A fast Fourier transform (FFT) was used to enter the frequency domain for line-by-line analysis of the frequency response.

In order to be sure that the analyzed points did indeed correspond to parietal points, the analysis was windowed from point 100 to point 128 so to analyze instead the anterior portion of the posterior wall where the retina is situated. That was how frequency response curve was obtained, line by line, for the window under consideration.

For each section, all of the lines were averaged. Averaging was then performed over ten sections, taken at random for each eye.

3D Imaging of the Retina

Images of the retina were acquired by the ultrasound microscope with linear scanning along the X and Y axes. The data obtained was processed in two different ways to improve image reproduction, seeking to obtain a presentation that is easily recognizable for the clinician.

The first presentation of the data used a C-scan representation providing a plane image of the back of the eye as explored by echography. By way of comparison, we studied various ways of obtaining an image of the macular region that could be understood by ophthalmologists familiar with angiographic type representations of the retina. The back of the eye is reproduced thereon in the form of a flat photograph, even though the retina is concave with an anterior opening.

On the basis of 3D echographic acquisition, the C-scan makes it possible to extract planes transverse to the X and Y axes. By selecting a window comprising a plurality of such parallel planes, the C-scan reduces the information to a single plane image, after using an operator of the maximum, minimum, average, or median type on the amplitude of the signal.

The second representation of the data made use of a silicon graphics workstation operating under Unix and AVS software. Processing followed the following sequence:

reading in the data;

averaging over 49 points and then reducing the data by retaining 1 value out of 7 so as to reduce the size of the images which were oversampled;

converting data values from a gray scale of −32000 to +32000, to a gray scale of 0 to 255;

thresholding: a threshold of 15 was applied to the values in the range 0 to 255 so as to show up zones of interest;

a morphological opening operation using a horizontal structure element having a length of 31 pixels so as to eliminate vitreous images associated with intravitreous bands coming into contact with the retina;

a morphological opening operation with a vertical structural element having a length of 3 pixels to eliminate artifacts associated with vitreo-retinal attachments;

filling in holes of size smaller than 200 for black objects (based on labelling pixels by adjacent regions and then eliminating small spots);

eliminating objects of size smaller than 500 pixels for white objects, with these two operations serving to eliminate small spots of black or white pixels so as to retain only the outline of the retina which represents the boundary between the vitreous cavity and the posterior wall of the eye;

a mathematical closing operation of cross-shape to reduce contour irregularity; and 3D display of the surface of the objects obtained in this way. The images were reproduced by using a color laser printer.

Histology

The six human eyeballs were sent to the anatomocytoplathology eye laboratory at the Hôtel Dieu Hospital in Paris.

All of the eyes had been fixed in Bouin's solution, half of them immediately after being removed and the other half after echographic analysis had been performed on the fresh eyeball without allowing more than 12 hours to pass between the eyeball being removed and being fixed.

The eyeballs were treated by being cut and included in paraffin and then semi-fine (2 $\mu$m thick) sections were made using an ultramicrotome (Reichart OMU).

The various sections were stained using HES and analysis was performed using an optical microscope.

While exploring the posterior segment, the following results were observed.

The possibility of using a 50 MHz probe focused at 25 mm (28 MHz at the focal length) enabled us to position the transducer on the pars plana of the various animal and then human eyeballs so as to lay the foundation for non-invasive in vivo exploration of the macula that can be used in ordinary practice.

The ultrasound beam initially passes through the peripheral wall of the eye, then through the entire vitreous cavity and finally reaches the posterior wall of the eye. By positioning the eyeball so as to expose the nasal pars plana facing the transducer, the posterior can be explored directly in the macular zone which is situated at the temporal side of the optic disk. The optic disk is a mark that is identifiable with 10 MHz echography, as at higher frequency.

The initial tests performed on the fixed pig eyeball served to display the posterior wall in spite of the poor quality of the retinal tissue after fixing. Nevertheless, the tests performed helped to adjust the various parameters of the system for acquiring echographic data so as to optimize the results of exploration on the human eyeball.

The best images were obtained with the 50 MHz Panametric probe focused at 25 mm, connected to the generator whose damping was set at 50 ohms, and power at 2 microjoules. The Lecroy oscilloscope performed averaging over 30 measurements per point.

The motors moved in 100-micron steps along the X axis and in 200-micron steps along the Y axis when 3D acquisition was started.

Since the average axial length of a human eyeball is 23.5 mm, positioning the transducer on the ora serrata made it possible to bring the focus of the probe onto the macular retina. Analyzing the sections made on eyeballs 1 and 2 compared with macular sections obtained by 10 MHz echography shows better resolution in the images obtained with the 50 MHz Panametrics probe.

Figure 1B:
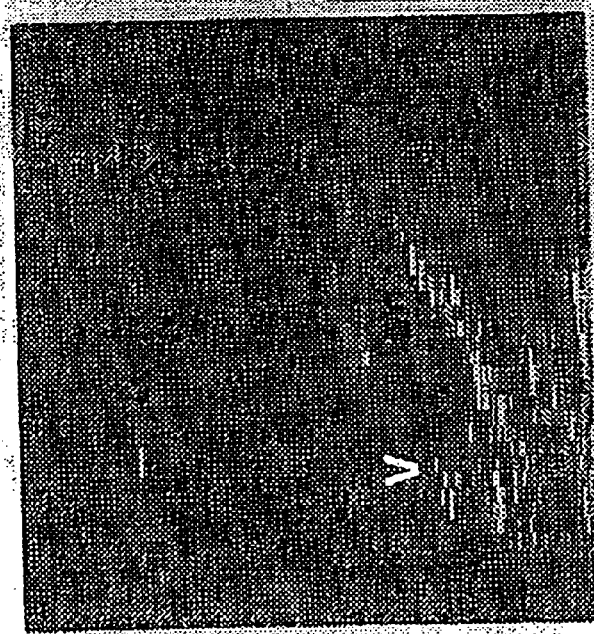

FIG. 1 is a comparison between the image of a conventional B-scan section at 10 MHz (FIG. 1A) where there can be seen in eyeball No. 1 that vitreous reshaping is present with slight undulations of the retinal wall.

The higher frequency macular image (FIG. 1B) shows one of the first images obtained with a retinal fold that can be seen at the bottom of the section. A fine band of vitreous body is attached to the retinal fold.

The images obtained on eyeballs 3, 4, 5, and 6 are even clearer.

Figure 2A:
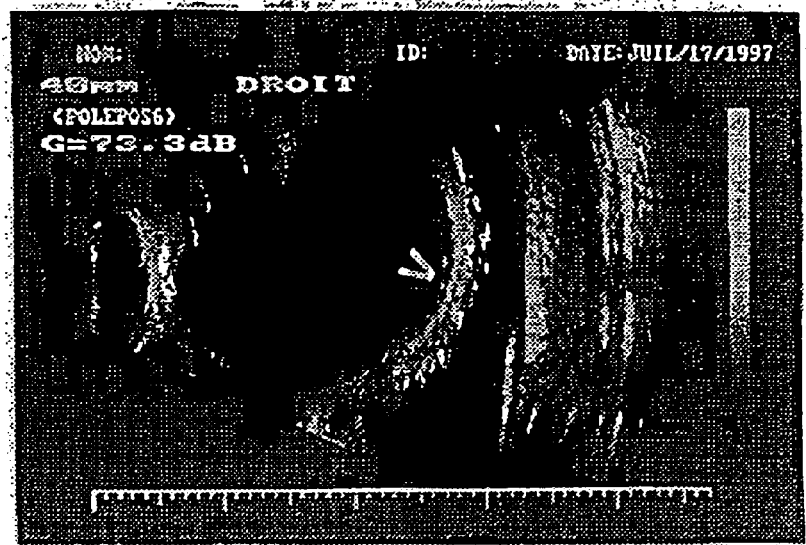
FIG. 2 shows a 10 MHz echographic section passing through the macular region of eyeball No. 6 with a small undulation of the posterior wall.

FIG. 2A shows a 10 MHz echographic section passing through the macular region of eyeball No. 6 with a small undulation of the posterior wall.

Figure 2B:

As shown in FIG. 2B, the high frequency section passing through the same zone shows more precisely the deformation of the posterior wall with the presence of vitreous traction that is undetected with conventional echography.

It should be observed that these echographic images were obtained with a high frequency probe covered in a film or membrane of plastics material, whereas the probe of the device presently sold for exploring the anterior segment makes use of transducers that are not protected from the immersion bath.

Analysis of the Frequency Response of the Retinal Signals

Given the emission frequency of the Panametrics probe (50 MHz) and its maximum frequency at its focus in serum (28 MHz), we set out to measure the maximum frequency actually found close to the focus after passing through the media of the eye. It is this frequency that determines the spatial resolution of images of the posterior segment. After thresholding at 100 radiofrequency lines and shifting the first point of the retina to zero, an FFT gave a mean curve of frequency responses for each retinal image.

Performing this operation on ten randomly-selected sections of each of the six eyeballs, gave a mean value of 21 MHz, which is slightly less than the 28 MHz from the same probe as measured at its focus. This change in signal frequency is due to the ultrasound wave passing through structures of the eye (limbic wall, and vitreous cavity whose attenuating collagen structure had been degraded by post-mortem reshaping associated with tissue autolysis and with freezing of the body).

Eyeballs 3 and 4 had a higher frequency response (22.033 MHz and 21.638 MHz): this might be because the vitreous humor was in a better state and therefore gave rise to less attenuation of the ultrasound beam.

This result shows that the ultrasound microscope used in our study makes it possible to obtain a frequency of 21 MHz at the posterior wall of the human eyeballs analyzed, i.e. at least twice the frequency presently found in conventional 10 MHz probes for which frequency attenuation of the signal is much smaller.

The 21 MHz obtained at the focus with our device enabled us to obtain resolution that was at least twice as good when exploring the posterior wall of the eye, in comparison with the resolution of a conventional 10 MHz device.

3D acquisition made it possible to apply the C-scan representation to the various human eyeballs thus giving a flat view of the back of the eye.

FIG. 3 shows various C-scans obtained while varying the amplitude parameter selected in the window. It is application of the median value to the amplitude of the signal that gives the best information. The example concerned relates to eyeball No. 3 for which we selected a window of 900 planes corresponding to the anterior portion of the posterior wall of the eye together with the retinal layer on its surface.

Figure 3C:
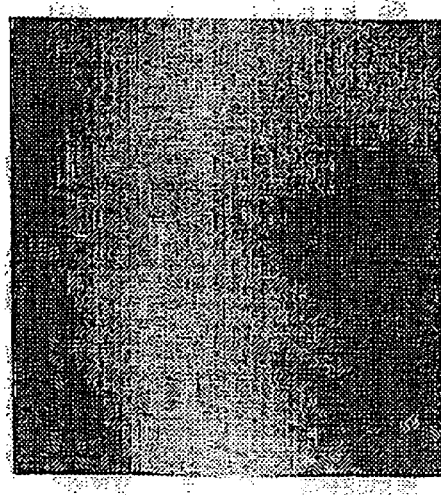
FIG. 3 shows various C-scans obtained while varying the amplitude parameter selected in the window.
Figure 3D:
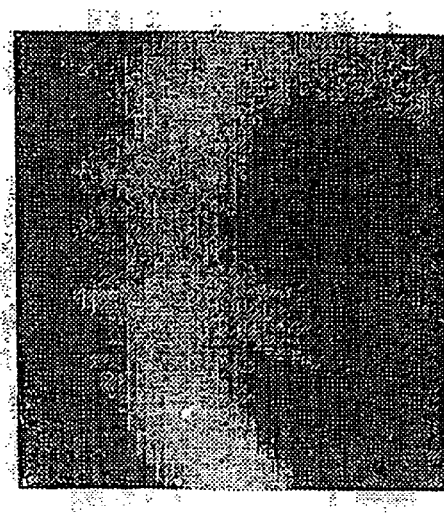
Figure 3A:
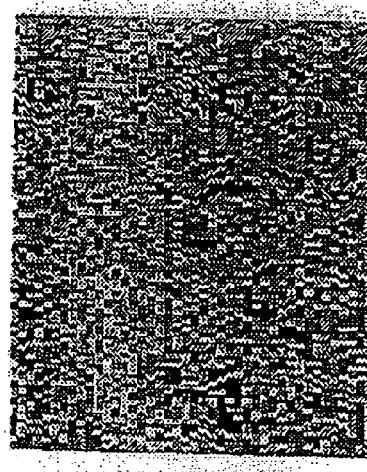

FIG. 3A shows the application of a minimum type operator which leads to an image that is difficult to interpret.

Figure 3B:
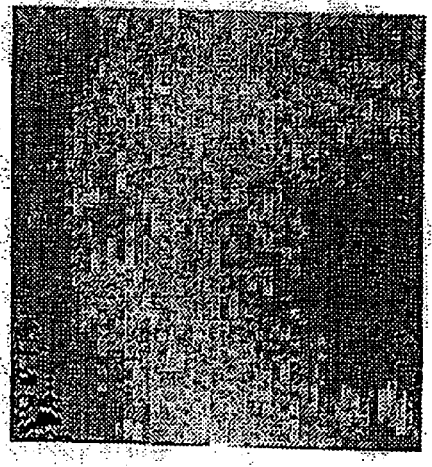

FIG. 3B corresponds to applying an operator of the maximum type on the same 900 planes, causing a fuzzy image to be appear.

FIG. 3C is the result of the averaging type operator which serves to identify the appearance of the back of the eye resembling observations made by ophthalmologists in everyday practice with various magnifying glasses. At the top of the image it is possible to identify a rounded hypo-echo-generating structure which corresponds to the optic disk. Starting from the optic disk, it is possible to see a "cast" that is more echo-generating and that extends obliquely downwards and to the left; this image corresponds to the largest retinal fold found in the various B-scans passing through this zone.

Of the representations obtained, FIG. 3D is the best for showing clearly and instructively the state of the macular retina. This image was obtained by applying a median type operator on the same 900 planes of the acquisition. The retinal fold and the optic disk appear almost real and highly comparable to clinical images and to conventional angiographs.

By using the C-scan, it is possible to select a window of planes situated at different depths so as to make it possible, for example, to study planes beneath the retina or the deep layers of the optic disk. This advantage enables the system to be highly complementary to angiographic exploration by giving information on the deep planes of the macula, regardless of the transparency conditions applying to the intervening media. For example, angiographs are difficult to interpret when there has been hemorrhage into the vitreous medium or into the surface layers of the retina.

One of the more advantageous applications may be exploring the submacular neovascular membranes associated with age-related macular degeneration (ARMD). This ever-more frequent and highly invalidating pathology is being subjected to highly promising novel surgical treatments in which the membranes are extracted by microscopic sub-retina dissection. Angiographic exploration coupled with echographic imaging at histological level will give the surgeon a better understanding of the shape, the extent, and the thickness of these membranes, while also identifying their sub-retinal relationships. This type of imaging will also make better appraisal possible of physiopathology.

Human eyeball No. 3 was selected to serve as a basis for 3D reconstruction; that was the eyeball having the most easily identified retinal fold.

Figure 4:
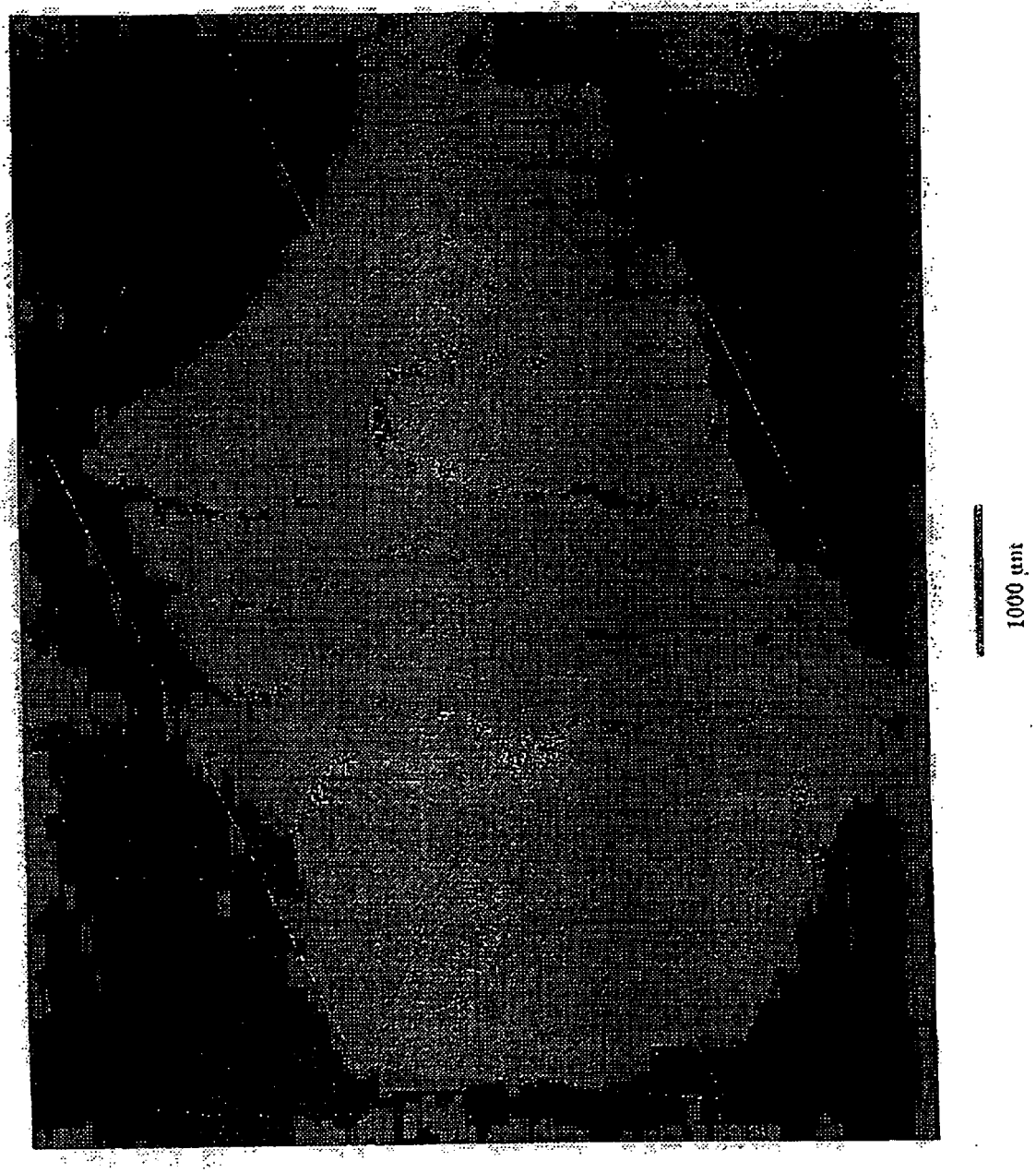
FIG. 4 shows the result of printing one of the 3D views as obtained after applying the AVS program.

FIG. 4 shows the result of printing one of the 3D views as obtained after applying the AVS program. It is possible to identify the retinal fold which forms very clear relief in front of the retinal plane. However its outlines are irregular and probably enlarged by imperfect segmentation between the retina and the vitreous humor.

The interest of such 3D imaging is to give a more overall view of pathology of the posterior segment, particularly when it gives rise to thickening, since measuring volume is easy. Clinical applications will be quickly directed to age-related macular degeneration which is very frequent, and also to tumors of the posterior segment. With tumors, the advantage of our system is to conserve all of the information from the radiofrequency signal so as to study not only the volume and the extensions of these lesions, but also to characterize the tissue thereof by analyzing the attenuation and diffusion parameters of the ultrasound.

The histological analysis of the various human eyeballs showed much macroscopically visible autolytic spoiling in all of the eyeballs, with extensive necrosis of the retina that had given rise to a loss of anterior retinal substance, but the retina remains visible at the posterior pole where it appears to have thickened with folding, and zones of separation due to artifacts. It comprises nuclear layers between highly autolyzed layers.

Nevertheless, this stack of layers makes it possible to recognize the retina without difficulty. The folded layers of the retina and the focus thickening of the retina can be seen on either side of the retina adjacent to the optic disk, the only part to have resisted autolysis, and to the opening of the eye.

The choroidian plane can clearly be seen, running on from the ciliary plane, where the choroid is a relatively well preserved vascular and fibrous structure that is easily recognized.

Figures 5A, 5B:
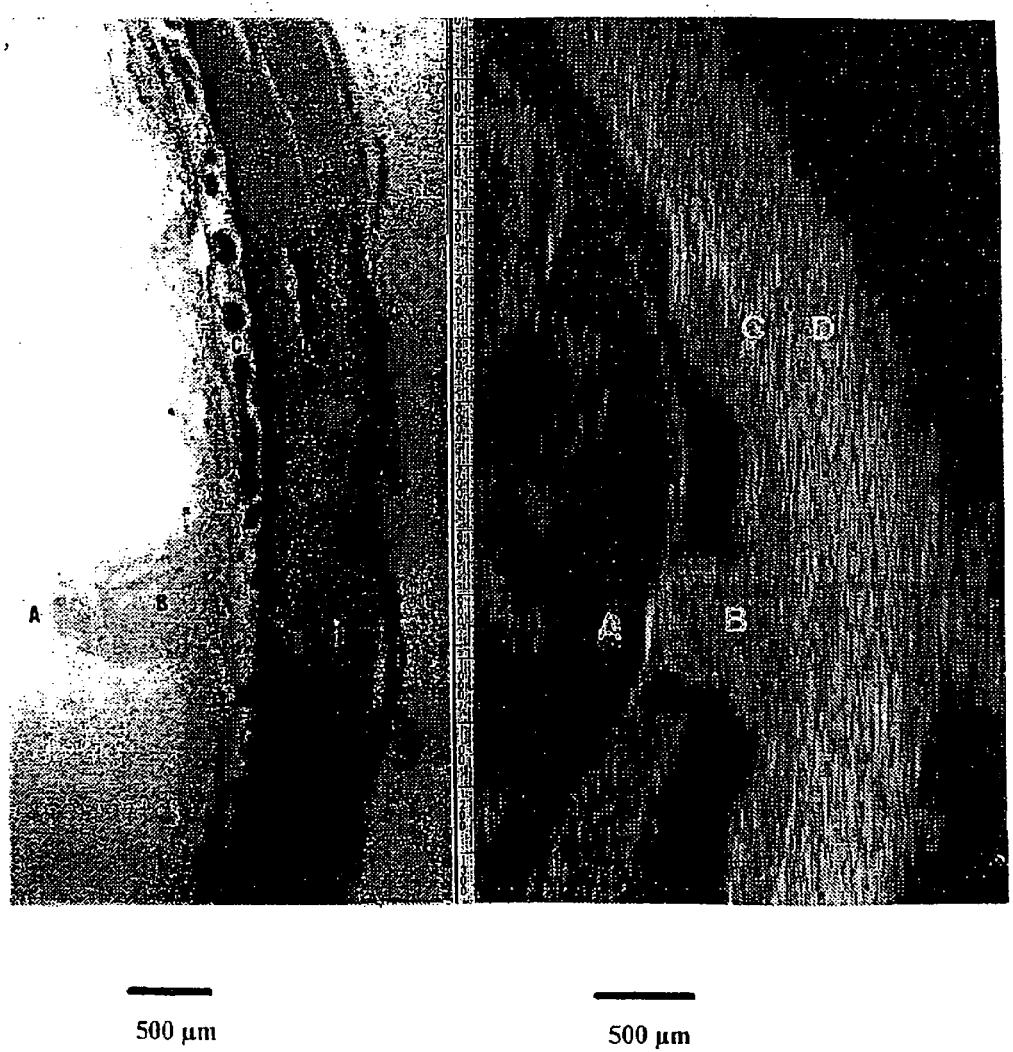
FIG. 5 shows an example of comparing a macroscopic histological section of eyeball No. 3 (left-hand picture) with an ultrasound microscopic section (right-hand picture) passing through the same macular region.
Figure 6:
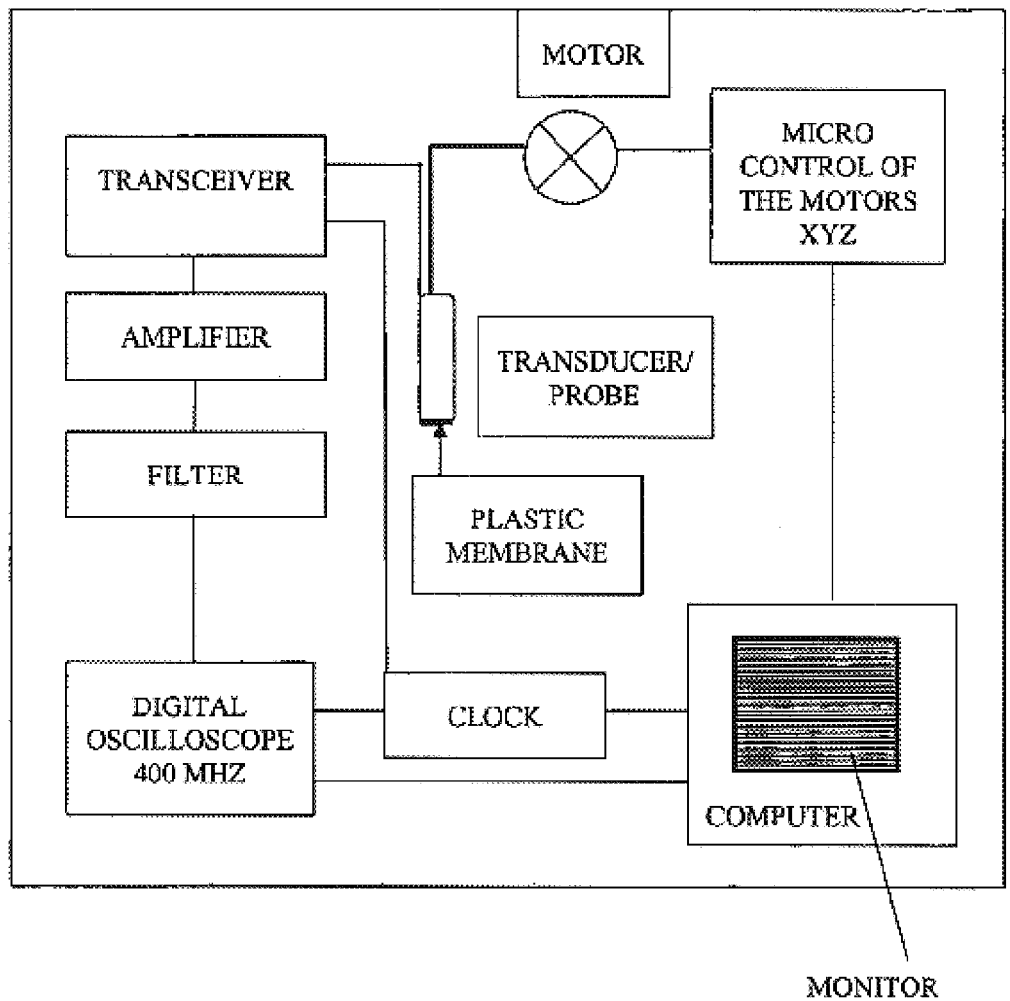
FIG. 6 is a block diagram showing the main parts of the system.

FIG. 5 shows an example of comparing a macroscopic histological section of eyeball No. 3 (FIG. 5A) with an ultrasound microscopic section (FIG 5A) passing through the same macular region.

In the histological section, there can be seen a clear retinal fold (A) and then towards the top of the picture, a series of less prominent retinal folds. The sub-retinal space is occupied by necrotic material (B) and then by the choroid (C) which is recognizable by its conserved vascular structure. The scleral wall (D) of striped appearance does not present any anomalies.

In the echographic picture, there can be seen the same retinal fold (A) which appears in the form of an echo-generating margin, followed by the same undulations as in the histological section. Beneath the retina, there is a small space that generates less echo (B), corresponding to the sub-retina necrosis. Further back, there is an arcuate layer that generates more echo (C), correspond to the choroid, and then the scleral wall which appears to have medium echo-generating ability (D).

The various retinal folds recognized by echography thus correspond to the postmortem retinal folds with sub-retinal necrosis, but with the appearance of the choroid being preserved.

When the histological sections are compared to the B-scans of the ultrasound microscope, it can be seen that it is possible to recognize the retinal layer proper quite clearly, measured histologically at about 400 microns, when the retina is separated from the choroid by the sub-retinal necrotic material which can be seen to generate less echo.

This resolution, compared with the resolution of 10 MHz probes, represents considerable progress provided by the present invention.

It makes it possible to analyze macular thickenings including retinal folds, e.g. ARMD, as found on the human eyeballs we took, giving rise to a good echographic model.

The possibility of achieving better exploration of this region of the eye which is essential for good quality of visual perception leads to the hope that this technique will be used more and more frequently firstly as means merely for iconographing various macular pathologies, and subsequently as means for obtaining quantitative analysis of echographic information coming from said region of the eye having a high density of photoreceptors.

What is claimed is:

1. A method for making a device for echographic exploration of tissues or organs of a human or animal body, comprising:
providing an ultrasound transducer having a nominal excitation frequency greater than 20 MHz and a focal length of about 20 mm to about 25 mm, said transducer adapted for deep penetration echographic exploration of tissues or organs of the human or animal body.

2. A method according to claim 1, wherein the focal length of the ultrasound transducer is approximately 25 mm.

3. A method according to claim 1, wherein the tissues or organs explored comprise eyeballs.

4. A method as claimed in claim 3, wherein the tissues or organs explored comprise a posterior segment of the eyeball.

5. A method as claimed in claim 4, wherein the tissues or organs explored comprise a macular region of the posterior segment of the eyeball.

6. A method as claimed in claim 1, wherein the tissues or organs explored comprise at least one of oculomotor muscles, eye socket fat, and an optic nerve.

7. A method for exploring tissues or organs of a human or animal body, comprising:
exploring the tissues or organs of a human or animal body with an ultrasound transducer having a nominal excitation frequency greater than 20 MHz and a focal length of about 20 mm to about 25 mm, to achieve deep penetration echographic exploration.

8. A method according to claim 7, further comprising the step of moving the ultrasound transducer over a pars plana to avoid an ultrasound beam being absorbed by a lens of the eye.

9. A method according to claim 7, further comprising the step of covering the ultrasound transducer with a membrane of plastic material.

10. A method according to claim 7, wherein the nominal excitation frequency is between 50 MHz and 80 MHz.

11. A method according to claim 7, wherein the focal length is approximately 25 mm.

12. A method according to claim 7, wherein the tissues or organs explored comprise eyeballs.

13. A method according to claim 12, wherein the tissues or organs explored comprise a posterior segment of the eyeball.

14. A method according to claim 13, wherein the tissues or organs explored comprise a macular region of the posterior segment of the eyeball.

15. A method according to claim 7, wherein the tissues or organs explored comprise at least one of oculomotor muscles, eye socket fat, and an optic nerve.

16. A method according to claim 7, wherein the ultrasound transducer comprises a probe, and the method further comprises the step of moving the probe in a vicinity of an anterior wall of an eye.

17. A method according to claim 16, wherein the moving step moves the probe along two orthogonal axes.

18. A method according to claim 17, further comprising the step of focusing the ultrasound transducer along a third axis orthogonal to the two orthogonal axes.

19. A method according to claim 16, wherein the moving step moves the probe in an arcuate displacement.

20. A method according to claim 7, further comprising the step of focusing the ultrasound transducer with an electronic focusing system.

21. A device for deep penetration echographic exploration of tissues or organs of the human or animal body, the device comprising:

a transceiver system operating in the range 20 MHz to 200 MHz; and an ultrasound transducer coupled to the transceiver system, said transducer having a focal length of about 20 mm to about 25 mm.

22. A device according to claim 21, wherein the ultrasound transducer comprises a probe, and the device further comprises a motor to move the probe in a vicinity of an anterior wall of an eye.

23. A device according to claim 22, wherein the motor displaces the ultrasound transducer along two orthogonal axes.

24. A device according to claim 23, wherein the ultrasound transducer is focused along a third axis orthogonal to the two orthogonal displacement axes.

25. A device according to claim 22, wherein the motor moves the transducer in an arcuate displacement.

26. A device according to claim 21, wherein the device further comprises an electronic focusing system to focus, without moving, the ultrasound transducer.

27. A device according to claim 21, further comprising a plastic membrane covering the ultrasound transducer.

28. A device as claimed in claim 21, wherein the focal length of the ultrasound transducer is approximately 25 mm.

29. A device as claimed in claim 21, further comprising:
a system to amplify and store a radio frequency signal as back-scattered after exploration; and
a system to record an amplified signal.

30. A device as claimed in claim 21, further comprising:
a system to amplify and store a radio frequency signal as back-scattered after exploration; and
a system to process an amplified signal in a form of an image.

31. A device as claimed in claim 21, further comprising:
a system to amplify and store a radio frequency signal as back-scattered after exploration; and
a system to process an amplified signal in order to perform tissue characterization.

32. A method for making the device of claim 21, comprising:
providing an ultrasound transducer having a nominal excitation frequency greater than 20 MHz and a focal length of about 20 mm to about 25 mm that is capable of focusing on the macular region of the eye said transducer adapted for deep penetration echographic exploration of tissues or organs of the human or animal body.

33. A device for deep penetration echographic exploration of tissues or organs of the human or animal body, the device comprising:
a transceiver system operating in the range 20 MHz to 200 MHz; and
an ultrasound transducer coupled to the transceiver system, said transducer having a focal length of about 20 mm to about 25 mm and capable of focusing on the macular region of the eye.

34. A method for making a device for echographic exploration of tissues or organs of a human or animal body, comprising:
providing an ultrasound transducer having a nominal excitation frequency greater than 20 MHz and a focal length of about 20 mm to about 25 mm that is capable of focusing on the posterior wall of the eye, said transducer adapted for deep penetration echographic exploration of tissues or organs of the human or animal body.

35. A device for deep penetration echographic exploration of tissues or organs of a human or animal body, the device comprising:
a transceiver system operating in the range 20 MHz to 200 MHz; and
an ultrasound transducer coupled to the transceiver system, said transducer having a focal length capable of focusing on the posterior wall of the eye and of about 20 mm to about 25 mm.

* * * * *